(12) United States Patent
Arnold

(10) Patent No.: US 6,444,150 B1
(45) Date of Patent: Sep. 3, 2002

(54) METHOD OF FILLING A MICROCHANNEL SEPARATION COLUMN

(75) Inventor: Don W. Arnold, Livermore, CA (US)

(73) Assignee: Sandia Corporation, Livermore, CA (US)

( * ) Notice: Subject to any disclaimer, the term of this patent is extended or adjusted under 35 U.S.C. 154(b) by 0 days.

(21) Appl. No.: 09/161,321

(22) Filed: Sep. 25, 1998

(51) Int. Cl.[7] .............................................. B29C 67/00
(52) U.S. Cl. .................... 264/69; 264/113; 264/122; 264/138; 264/250; 264/254; 264/255; 264/443; 210/656; 210/661
(58) Field of Search .................... 264/69, 570, 573, 264/267, 138, 250, 443, 254, 255, 113, 122; 210/656, 198.2, 510.1, 661

(56) References Cited

U.S. PATENT DOCUMENTS

| | | | | |
|---|---|---|---|---|
| 4,578,193 A | * | 3/1986 | Sheperd | 210/656 |
| 4,793,920 A | * | 12/1988 | Cortes et al. | 210/198.2 |
| RE35,185 E | * | 3/1996 | Kolesinski | 526/263 |
| 5,637,135 A | * | 6/1997 | Ottenstein et al. | 96/101 |
| 5,679,255 A | * | 10/1997 | Cortes et al. | 210/656 |
| 5,997,746 A | * | 12/1999 | Valaskovic | 210/656 |

* cited by examiner

*Primary Examiner*—Jan H. Silbaugh
*Assistant Examiner*—Edmund H. Lee
(74) *Attorney, Agent, or Firm*—Donald A. Nissen

(57) ABSTRACT

A method for packing a stationary phase into a small diameter fluid passageway or flow channel. Capillary action is employed to distribute a stationary phase uniformly along both the length and diameter of the flow channel. The method disclosed here: 1) eliminates the need for high pressure pumps and fittings and the safety hazards associated therewith; 2) allows the use of readily available commercial microparticles, either coated or uncoated, as the stationary phase; 3) provides for different types of particles, different particle sizes, and different particle size distributions to be packed in sequence, or simultaneously; 4) eliminates the need for plugging the flow channel prior to adding the stationary phase to retain the packing particles; and 5) many capillaries can be filled simultaneously.

8 Claims, 5 Drawing Sheets

US 6,444,150 B1

METHOD OF FILLING A MICROCHANNEL SEPARATION COLUMN

STATEMENT OF GOVERNMENT INTEREST

This invention was made with Government support under contract no. DE-AC04-94AL85000 awarded by the U.S. Department of Energy to Sandia Corporation. The Government has certain rights in the invention.

CROSS-REFERENCE TO RELATED APPLICATIONS

Not applicable

BACKGROUND OF THE INVENTION

The present invention pertains generally to a method for packing chromatographic columns with a stationary phase and particularly, to a method for packing capillary columns and microchannels.

Chromatography is a method for chemical analysis in which a sample (analyte) consisting of multiple components is introduced into a chromatographic column. As the sample flows through the chromatographic column the individual components of the mixture are separated into distinct bands that are detected near the exit end of the column. The chemical separations are carried out by flowing the sample (analyte) past an immobilized material (the stationary phase) inside the chromatography column. Separation is governed by the dynamic partitioning of the various components of the sample between the analyte and the stationary phase. Control of the separation can be achieved by adjusting the composition of the analyte or the stationary phase or both to influence analyte partitioning.

Conventionally, the stationary phase has been small silica spheres coated with one of a variety of chemical compounds to optimize the chemical separation efficiency. In general, reduction of the chromatography column diameter offers several advantages such as reduced solvent consumption and reduced sample volume requirements. Several chromatography-based analytical methods using miniaturized or capillary columns have been developed. Micromachining techniques have been used to create microchannels 10 to 30 $\mu$m wide that can be used for capillary electrophoresis (cf. D. J. Harrison et al., *Science*, 261, 895, Aug. 13, 1993). However, for packed capillary column methods, such as capillary electrochromatography (CEC) and size exclusion chromatography (SEC), as the column diameters decrease it becomes more difficult to pack the column in a uniform and reproducible way. Irregularities in the uniformity of the stationary phase, both along the length and across the diameter of the column, reduces the efficiency of the chemical separation.

Methods of column packing depend principally on the mechanical strength of the packing, its particle size and particle size distribution, and the diameter of the column to be packed. Conventional column packing methods, such as dry packing, typically used for particles greater than about 20 $\mu$m in diameter, are not useful for small capillary columns or microchannels that typically have diameters in the range of tens of microns. For particles between 1 and 20 $\mu$m in diameter slurry techniques can be used. In slurry packing the particles that form the bed are suspended as a slurry in an appropriate liquid or liquid mixture. Many liquids or liquid mixtures can be used to prepare the slurry, the principal requirement being that the liquid thoroughly wet the packing particles and provide adequate dispersion of the packing material. The slurry is then pumped into the column. However, as the diameter of the column or channel decreases it becomes necessary to apply higher pressures to force the slurry into and through the column and pressures of 200 to 500 atm are not uncommon. In addition to the obvious hazard of having to work with very high pressures exerted on relatively thin walled tubes, there are other disadvantages to this method of column packing. When the pumping pressure is released at the conclusion of the packing operation the restraining force on the particle bed is partially lost causing an expansion of the particle bed. Then, when the column is once again pressurized heterogeneities or irregularities, such as channels or dead volume, can occur in the particle bed.

Instead of pressure, electro-osmotic flow can be used to carry particles into the capillary from a reservoir of particles suspended in solution. To generate this flow, voltages of from 10 to 30 kV are applied across the capillary. A porous plug or other particle retaining means must be installed at the exit end of the capillary prior to filling to prevent the particles from passing directly through the channel during the filling operation. This method of packing capillary columns suffers the disadvantages of needing very high voltages and a pre-formed porous plug for operation. In general, these methods often do not generate packed beds with optimal uniformity and requires relatively complicated hardware to perform.

Various other approaches have been proposed for introducing a stationary phase into microchannels, in general, and capillaries, in particular, in order avoid the problems associated with pressurized slurry packing. Among these are, coating very small diameter ($\approx$=2–5 $\mu$m) microchannel walls, fabricating microstructures, such as "columns" or "posts", within the microchannels itself to serve as the stationary phase, and using xerogels to fill the microchannels.

In prior art processes that employ a packed column for chromatographic analysis, filling a capillary or microchannel with a stationary phase requires that a porous plug or means for retaining the stationary phase within the capillary (while still permitting fluid flow) be put in place prior to the step of filling. This can be a very difficult operation, generally requiring that the material that will composes the porous plug be positioned somehow at the appropriate place in the capillary column. The material is sintered to form a plug that will retain structural integrity as well as a high degree of porosity, while simultaneously fusing the plug to the wall of the capillary.

What is needed is a simple method for filling capillaries and/or microchannels with a stationary phase that eliminates the need for high pressure pumping and forming a retaining means within the capillary column prior to filling with the stationary phase.

SUMMARY OF THE INVENTION

It is an object of the present invention to provide a method for packing a stationary phase into a small diameter fluid passageway or flow channel, which can be a microchannel or a capillary, so that the stationary phase is uniformly distributed along both the length and diameter of the flow channel. It is a further object to eliminate the need for forming a porous plug or some other particle retaining means in a flow channel prior to adding the stationary phase. In particular, the present invention is directed toward a method for packing a stationary phase (generally a dielectric material which can or cannot be porous) into flow channels useful for micro-scale high pressure liquid chromatography (HPLC) or capillary electrochromatography (CEC).

The novel method disclosed here is designed to fill flow channels of various materials, whose internal dimensions can be on the order of tens to hundreds of microns, with a uniform distribution of a stationary phase comprising particles of various materials and sizes. The present invention overcomes the well-known and significant deficiencies of prior methods of column packing by causing a suspension of the particles, comprising the stationary phase in an appropriate liquid, to be transported through a flow channel by capillary action. Upon reaching the end of the flow channel the liquid can either evaporate, or flow into a receiving reservoir, leaving the non-volatile stationary phase behind, thereby uniformly filling the flow channel with the desired stationary phase.

The advantages of the method disclosed here are: 1) it eliminates the need for high pressure pumps and fittings and the safety hazards associated therewith for the introduction of a stationary phase into a capillary column; 2) it allows the use of readily available commercial microparticles, that can be coated or uncoated, as the stationary phase for performing chemical separations; 3) different types of particles, particle sizes, and particle size distributions can be packed in sequence, or simultaneously, thereby providing for more complex separations schemes; 4) there is no need for providing means for plugging the flow channel with a porous plug or other particle retaining means to retain the stationary phase prior to adding the stationary phase; and 5) many capillary columns can be filled simultaneously.

BRIEF DESCRIPTION OF THE DRAWINGS

These drawings include the following figures, with like numerals indicating like parts.

DETAILED DESCRIPTION OF THE INVENTION

Figure 1:
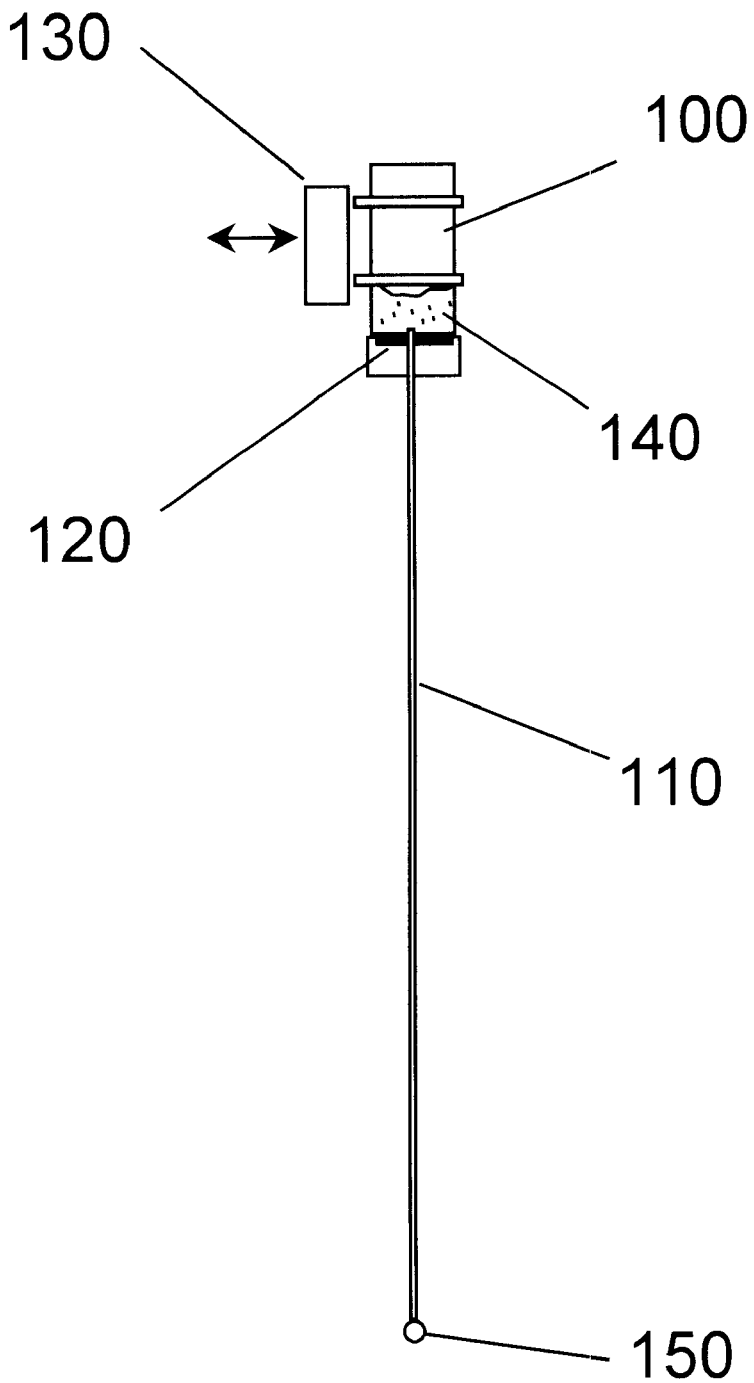
FIG. 1 illustrates a method of packing a capillary according to the present invention.

The present invention is directed toward a novel method for filling or packing small diameter fluid flow channels, such as microchannels or capillaries, with a stationary phase such that the stationary phase is distributed uniformly both along the length and the diameter of the fluid flow channel. The inventive method described here relies on capillary action to transport a suspension of a particulate solid phase, which can subsequently act as a stationary phase in a chemical separation scheme, into a fluid flow channel. When the suspension reaches the end of the flow channel, the liquid suspending agent can either evaporate, or flow into a receiving reservoir, leaving the particulate phase behind, thereby filling the flow channel with the desired stationary phase. The terms "stationary phase" and "column packing" are considered to be synonymous and will be used interchangeably throughout the description of the invention and various embodiments thereof.

It is well known in the chemical arts that the rise or fall of liquids in capillary tubes (tubes having internal diameters generally on the order of tens to hundreds of microns) is the direct result of the pressure differential which exists across any curved surface, the pressure being greater on the concave side than on the convex side. If the force of adhesion between the liquid and the capillary walls is greater than the force of cohesion between the liquid molecules themselves the contact angle the liquid makes with the capillary walls will be less than 90° and the liquid is said to "wet" the capillary walls and a concave meniscus is formed. In order to balance the pressure differential the liquid will rise in the capillary tube until pressure equilibrium is reached. The height that the liquid will rise in the tube is given by the equation $$h = \gamma 2\cos\theta/g\rho r \qquad 1)$$

wherein;

$\gamma$ is the surface tension of the liquid, h is the height to which the fluid rises in the tube, g is the gravitational constant, r is the radius of the tube, $\rho$ is the density of the liquid, and $\theta$ is the angle the surface of the liquid makes with the wall of the tube, the wetting angle. For liquids that wet the capillary walls the wetting angle is typically nearly zero, thus $\cos\theta=1$ and equation 1 can be approximated by the expression $$h \cong 2\gamma/g\rho r \qquad 2)$$

It can be readily seen from equation 2 that, providing the liquid wets the tube surface, the height that the liquid rises in a tube varies inversely as the radius of the tube and the density of the liquid and directly as the surface tension. It should be noted that capillary action can take place in the horizontal as well as the vertical dimension.

As disclosed herein, suspensions of solid particles in a suitable liquid are subject to capillary forces and, thus can be transported through a fluid passageway, which can be a capillary tube or a microchannel. For the purpose of describing the invention disclosed herein, the term microchannel, as used hereinafter, will refer to a fluid passageway, flow channel, or capillary whose internal dimensions are on the order of tens to hundreds of microns and can have an arbitrary cross-sectional geometry, in addition to the circular crosssection conventionally associated with capillaries.

The principle of the present invention will now be illustrated by reference to two embodiments which are incorporated into and form part of this invention. These embodiments only serve to illustrate the invention and are not intended to be limiting. Modifications and changes may become apparent to those skilled in the art, however, it is intended that the invention be limited only by the scope of the claims.

Referring now to FIG. 1, a container 100 containing a suspension of particles 140 to be packed in capillary 110 as the stationary phase, can be attached to the capillary by means of a septum 120. Other means of connecting capillary 110 can be used if they provide a leak resistant seal with capillary 110. The suspension was prepared by adding a weighed quantity of the particulate material that would comprise the column packing to a liquid. Typically, a concentration of about 5 to 10 mg/mL is preferred, depending upon the type of particle selected. Any liquid can be used as the suspending vehicle providing it does not react with the particles, however liquids having a high vapor pressure and low viscosity, such as methyl alcohol, acetonitrile, acetone, pentane, ethyl ether, hexane, or pentyl ether are preferred. Selection of a solvent can also depend upon the size of the particles chosen to be used as the stationary phase. The change in surface to volume ratio is significant in the range of sizes typically used as the stationary phase (0.3 $\mu$m to 5 $\mu$m) and can strongly affect the ability to successfully suspend the particles. In those instances where the solvent does not wet the particles adequately it is sometimes necessary to add a small volume of a less volatile liquid, such as water, to achieve adequate particle suspension. By way of example, it has been found that 2.5 $\mu$m non-porous silica particles and peptide coated particles are difficult to suspend without the addition of small quantities of water. The use of such liquids disadvantageously increases the time to fill the capillary channel due to the lower evaporation rate.

To counter the effects of gravitational settling in container 100 and to assist in suspending the particles, it can be desirable to provide an agitation source 130 coupled with container 110 to ensure particles remain in suspension. The container agitation can vary over a large range of frequencies to take advantage of different mechanical agitation principles. Direct mechanical agitation, using a frequency of between about 50 to 150 Hz depending on the resonant frequency of the liquid reservoir, can be used to maintain the particles in suspension. The resonant frequency depends upon the mass load on the agitator and will vary depending upon the mechanical setup. Higher frequencies ($\approx$40 kHz) can also be used to excite ultrasonic agitation in the solution directly.

Immediately upon connection of container 100 to capillary 110 particle suspension 140 begins to travel down capillary 110 by capillary action. At some later time, depending upon the length of the capillary and the viscosity of suspending liquid, a droplet 150 will appear at the opposite end of capillary 110 signaling that the suspension has traversed the length of the capillary. At this time the suspending liquid evaporates from the surface of the droplet leaving behind a solid plug of the packing material. In this way, the packing material forms its own porous plug, or retention means, eliminating the need for the separately formed frit conventionally employed for packed columns.

Although the inventive method does not require a porous plug or particle retaining means be installed in the capillary column prior to addition of column packing for to preventing particles of the column packing material from being forced from the column under normal operating conditions it has been found advantageous subsequent to filling the capillary column with the packing material to form a porous plug at the ends of the column. The porous plugs are formed by heat sintering particles of the column packing material at appropriate positions along the column. Two porous plugs are typically formed at each end of the column to fully restrict movement of the particles during operation of the column. It is preferred that the step of sintering be performed while the column is under pressure to prevent particle movement in the event high thermal gradients are established during the sintering process. Pressures of 300–350 atm. are applied using a simple $\mu$HPLC pump. To prevent particles of column packing material from being expelled during the pressurization step, it has been found useful to attach a blocking capillary to the low pressure end of the capillary column. It is preferred that the attachment be a low "dead volume" connector such as a piece of Teflon tubing which permits the blocking capillary to be disposed directly against the low pressure end of the capillary column. The blocking capillary can assume a variety of forms but the two most preferred forms are either 1) a capillary whose inner diameter is smaller than the diameter of the particles used in the packing of the column or 2) a small segment of capillary with a frit formed at the end which can be placed at the outlet of the column being prepared.

Figure 2:
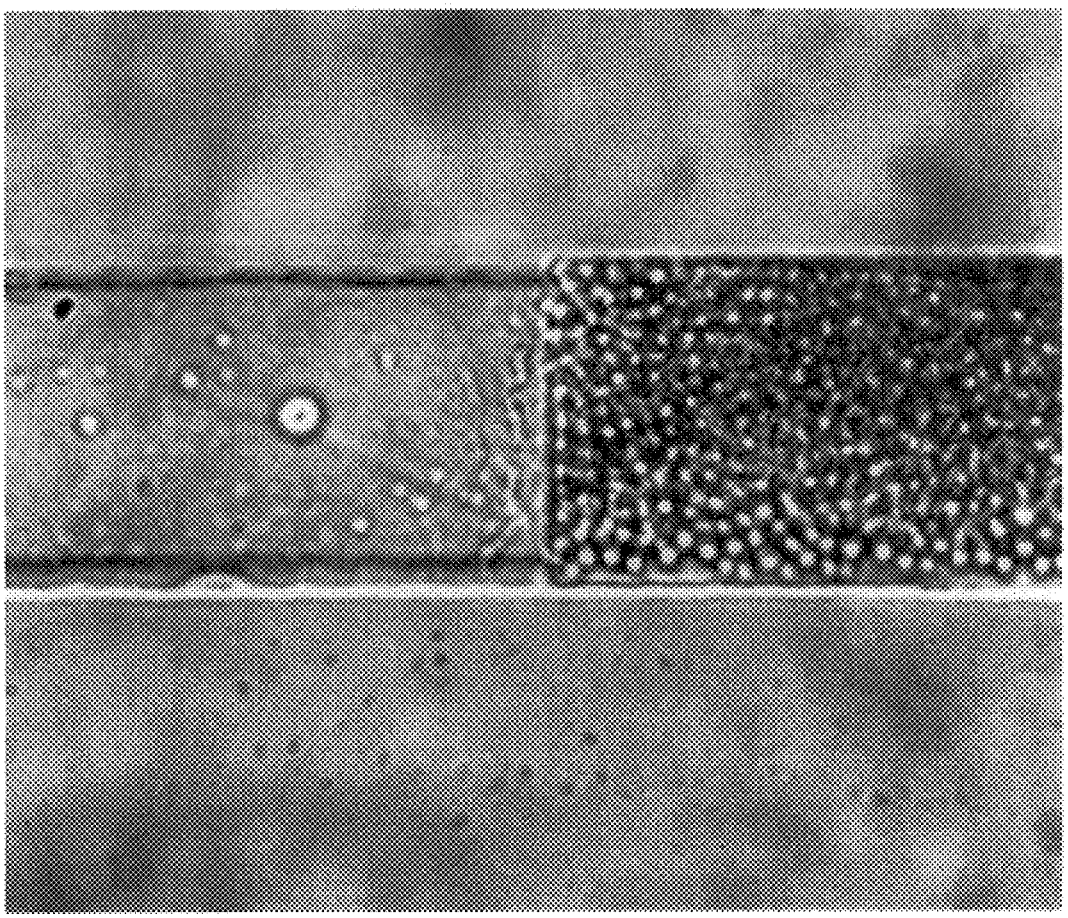
FIG. 2 shows a micrograph of a 100 $\mu$m capillary column filled with 3 $\mu$m particles using the inventive method.

Capillary action continues to draw the liquid phase through the capillary tube carrying with it the suspended particles which gradually fill up the capillary tube is filled with the particulate packing material. Using the method described here columns as long as 50 cm, having internal diameters of 100 $\mu$m have been packed with 5 $\mu$m diameter particles. Particles having a diameter less than 0.5 $\mu$m are readily packed to a length of more than 15 cm. Smaller particles, down to 0.2 $\mu$m have also been packed by the inventive method. Typically, the column lengths for 3 $\mu$m particles are on the order of 30 cm. Likewise, 75 $\mu$m and 50 $\mu$m diameter columns have been filled successfully using the inventive method. Microscopic examination of a capillary tube packed in this manner shows the particles to be uniformly distributed throughout the length of the capillary with no evidence of voids or channel, FIG. 2.

While the embodiment illustrated in FIG. 1 shows capillary tube 110 suspended from container 100 holding particle suspension 140, the reverse arrangement will also serve as a method for column packing well, wherein container 100 supports capillary 110 and particle suspension 140, in contact with capillary 110, rises up the capillary. However, this mode of column packing does not advantage of gravity and thus the height to which a column can be packed in this way is limited by eqn. 2.

It has also been found that a mixture of particle sizes can be loaded into the capillary column simultaneously. By way of example, a column was uniformly packed using a suspension containing a mixture of two sets of particles, having diameters of 0.6 $\mu$m and 3 $\mu$m respectively. The method described here also makes it possible to it multaneously pack a column with particles of different composition, such as coated and uncoated particles, which can or can not be of the same size. Moreover, using the inventive method, sequential packing of a column with particles of different size is also possible. A column packed with particles having a diameter of 1.0, 0.5, and 0.3 $\mu$m in sequence has been found to be useful for size exclusion chromatography.

While FIG. 1 illustrates the packing of one capillary column, the use of the method described here for simultaneously filling a plurality of capillary columns is contemplated.

Figure 3:
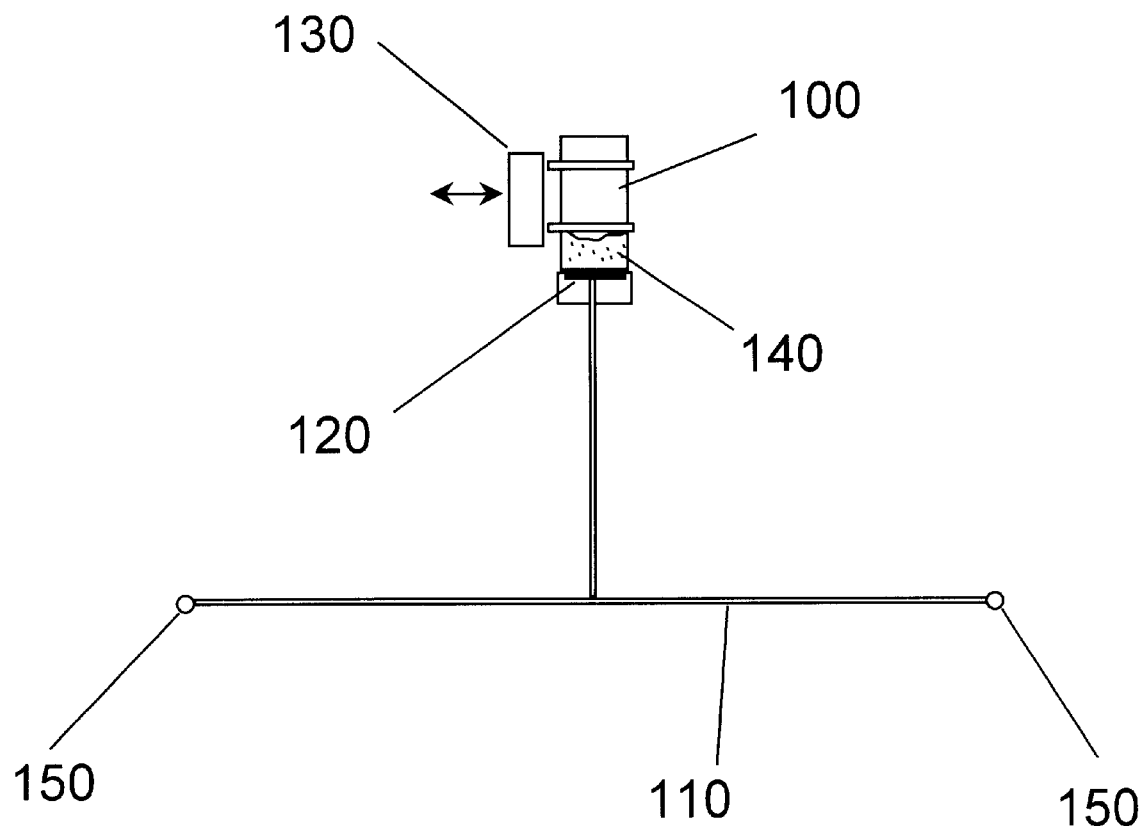
FIG. 3 shows an alternative mode of packing a capillary column.

One embodiment of the inventive method illustrated in FIG. 1 shows the capillary column being filled from one end. An obvious modification of the step of filling is to introduce particle suspension 140 at some point between the ends of capillary 110, as illustrated in FIG. 3. Capillary action then carries the particle suspension to both ends of capillary 110.

Figure 4:
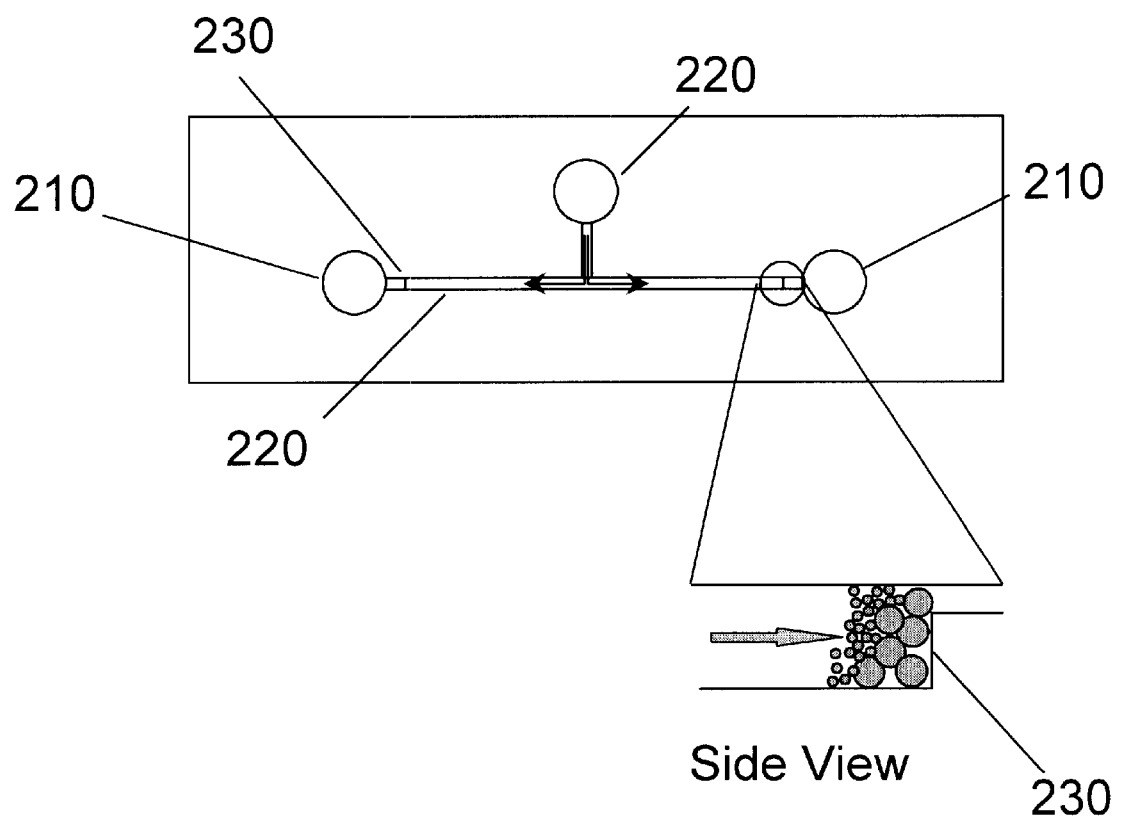
FIG. 4 illustrates packing a microchannel etched into a substrate by the method of the present invention and shows one embodiment of a particle retaining means.

Miniaturized systems for total chemical analysis (TAS) have been constructed from microchannels; these are flow channels typically about 100 $\mu$m wide and 20 $\mu$m deep, micromachined onto a silicon or glass substrate. As illustrated in FIG. 4, the present invention provides a method for uniformly filling these microchannels with a stationary phase for chemical separation and analysis.

Figure 5:
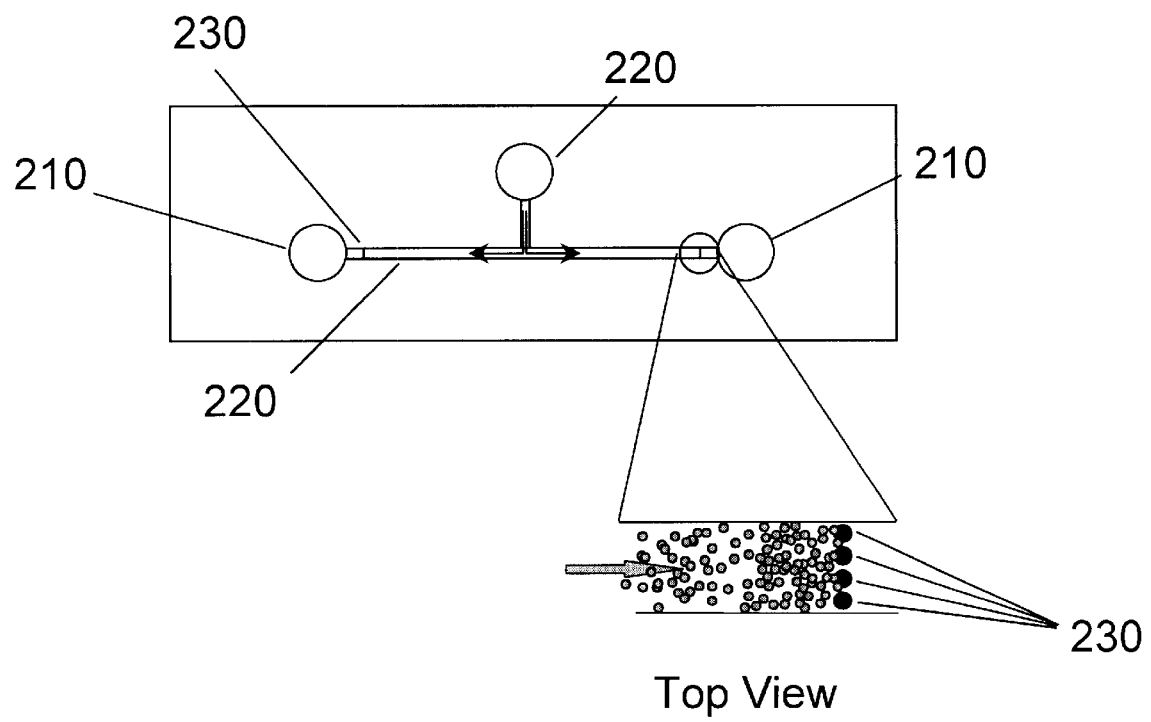
FIG. 5 shows an alternate embodiment of a particle retaining means for a microchannel.

A microchannel separation column 200, such as that illustrated in FIG. 4, can be provided with at least one means for receiving the liquid suspending agent, such as a fluid repository 210 at the end of microchannel separation column 200, or the ends of the separation column can simply be left open to allow the emerging liquid to evaporate. Microchannel column 200 is further provided with at least one means for introducing the particle suspension into the microchannel separation column that can be a fill reservoir 220 that holds a particle suspension and intersects and communicates with column 200 through a microchannel. Alternatively, microchannel column 200 can also be filled by means of a capillary tube connected to particle suspension, such as that shown in FIG. 1, wherein the capillary tube communicates directly with column 200 through fill reservoir 220. The linear extent of microchannel 200 is defined by a particle retaining means or barrier 230 fabricated at each end of the microchannel. Barriers 230 are fabricated in such a way as to allow the liquid suspending agent to flow past it but retain particles of the stationary phase from moving beyond the boundary defined at both ends of microchannel 200 by barriers 230. FIGS. 4 and 5 show magnified views of two separate embodiments of particle barriers useful for microchannel separation columns.

Filling of microchannel 200 with a stationary phase can be initiated by introducing a particle suspension into fill reservoir 220. Capillary action draws the particle suspension contained in fill reservoir 220 into microchannel 200. The suspending liquid flows past barriers 230, which retain the particles, and to the ends of column 200 where the liquid can either be collected in, a repository 210 or evaporate, leaving the particles behind. After microchannel 200 has been packed, repositories 210 and fill reservoir 220 can be sealed off.

As was the case with the embodiment illustrated in FIG. 1, it has been found to be useful to agitate he substrate during the step of filling the microchannel.

Microscopic examination of the microchannel packed by the inventive method shows the column packing particles to be uniformly distributed throughout the length of the microchannel with no evidence of voids or channel.

The above described arrangements of apparatus and the methods pertaining thereto are merely illustrative of applications of the principles of this invention and many other embodiments and modifications may be made without departing from the spirit and scope of the invention as defined in the claims.

I claim:

1. A method of filling a microchannel separation column by capillary action, comprising:

a) preparing a microchannel and a reservoir on a substrate such that the reservoir intersects the microchannel, the microchannel having a particle retaining barrier disposed at each end of the microchannel, wherein the particle barriers provide for retaining a particulate material while allowing liquid to flow past;

b) flowing a liquid suspension of the particulate material into the microchannel from the reservoir by capillary action such that the reservoir intersects the microchannel; and c) filling the length of the microchannel column between the particle retaining barriers with the particulate material.

2. The method of claim 1, further including the step of mechanically agitating the substrate.

3. The method of claim 1, wherein the liquid includes liquids having high vapor pressure and low viscosity.

4. The method of claim 3, wherein the liquids are selected from the group consisting of methyl alcohol, acetonitrile, acetone, pentane, ethyl ether, hexane, and pentyl ether.

5. The method of claim 1, wherein the particulate material includes a mixture of particulate material having different compositions.

6. The method of claim 1, wherein the particulate material consists of a mixture of different size particles.

7. The method of claim 1, wherein the microchannel is filled sequentially with particles of different sizes.

8. The method of claim 1, wherein the microchannel is filled sequentially with particles of different composition.

* * * * *